United States Patent [19]

Stettner

[11] Patent Number: 5,099,128
[45] Date of Patent: Mar. 24, 1992

[54] HIGH RESOLUTION POSITION SENSITIVE DETECTOR

[76] Inventor: Roger Stettner, 2441 Foothill La., Santa Barbara, Calif. 93105

[21] Appl. No.: 325,137

[22] Filed: Mar. 17, 1989

[51] Int. Cl.$^5$ .................................. H01L 27/146
[52] U.S. Cl. ...................... 250/370.11; 250/363.06; 250/363.10; 250/370.09; 357/30; 357/75
[58] Field of Search .............. 250/370.11, 370.09, 250/363.06, 363.10; 357/30 H, 30 G, 75

[56] References Cited

U.S. PATENT DOCUMENTS

| | | | |
|---|---|---|---|
| 3,358,145 | 12/1967 | Cashion et al. | 250/207 |
| 3,676,674 | 7/1972 | Zaviantseff | 250/363.01 |
| 3,749,911 | 7/1973 | Hoover et al. | 378/146 |
| 3,781,562 | 12/1973 | Singh | 250/360.1 |
| 3,869,615 | 3/1975 | Hoover et al. | 378/146 |
| 4,142,101 | 2/1979 | Yin | 250/363.01 |
| 4,250,385 | 2/1981 | Luderer et al. | 250/363.02 |
| 4,345,153 | 8/1982 | Yin | 250/369 |
| 4,404,469 | 9/1983 | Yin | 250/363.01 |
| 4,471,378 | 9/1984 | Ng | 358/110 |
| 4,472,728 | 9/1984 | Grant et al. | 357/30 |
| 4,521,688 | 6/1985 | Yin | 250/363.04 |
| 4,695,716 | 9/1987 | Tandon et al. | 250/211 R |
| 4,700,076 | 10/1987 | Dorman et al. | 250/370.09 |
| 4,791,300 | 12/1988 | Yin | 250/363.01 |

FOREIGN PATENT DOCUMENTS

| | | | |
|---|---|---|---|
| 61-258459 | 11/1986 | Japan | 357/75 |
| 2034148 | 5/1980 | United Kingdom | 250/363.10 |

OTHER PUBLICATIONS

"Gamma-Ray Imaging with a Rotating Hexagonal Uniformly Redundant Array", W. R. Cook et al., *IEEE*, Transactions on Nuclear Science, vol. NS-31, No. 1 (Feb., 1984), pp. 771-775.

*Primary Examiner*—Constantine Hannaher
*Attorney, Agent, or Firm*—Gottlieb, Rackman & Reisman

[57] ABSTRACT

A high spatial resolution gamma ray detector employs layers of scintillators, microchannel photomultipliers and sensors arrays of anodes to provide real time imaging of nuclear sources. Specific embodiments include a camera for detecting nuclear weapons within opaque containers and a device for discriminating exoatmospheric reentry vehicles from decoys.

45 Claims, 14 Drawing Sheets

FIG. 1a
HRCAM
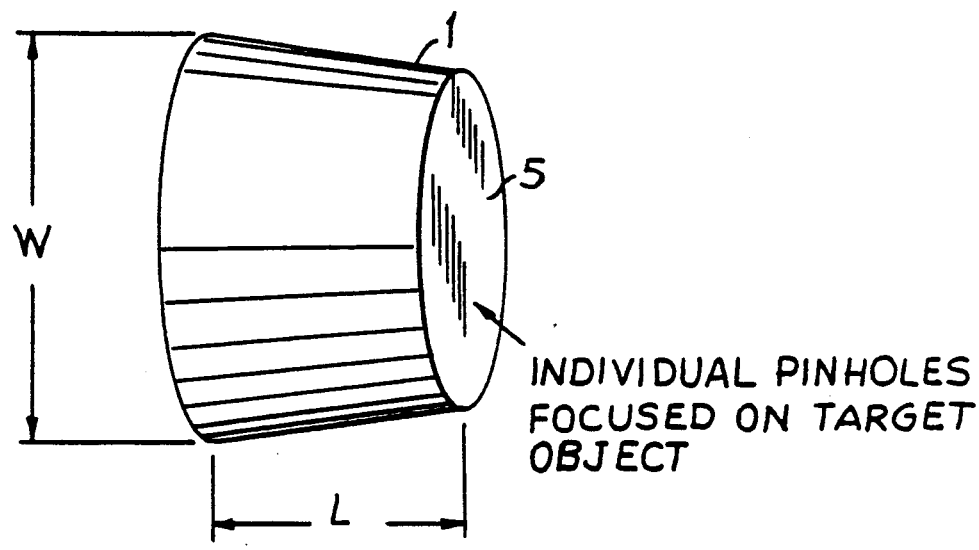
INDIVIDUAL PINHOLES FOCUSED ON TARGET OBJECT
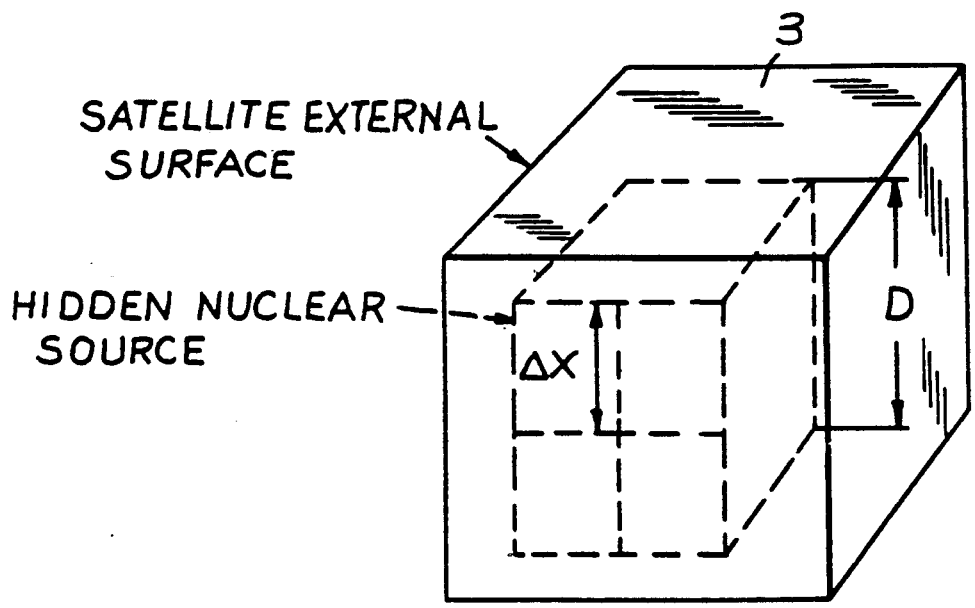
SATELLITE EXTERNAL SURFACE
HIDDEN NUCLEAR SOURCE
FIG. 1b FIG. 3a
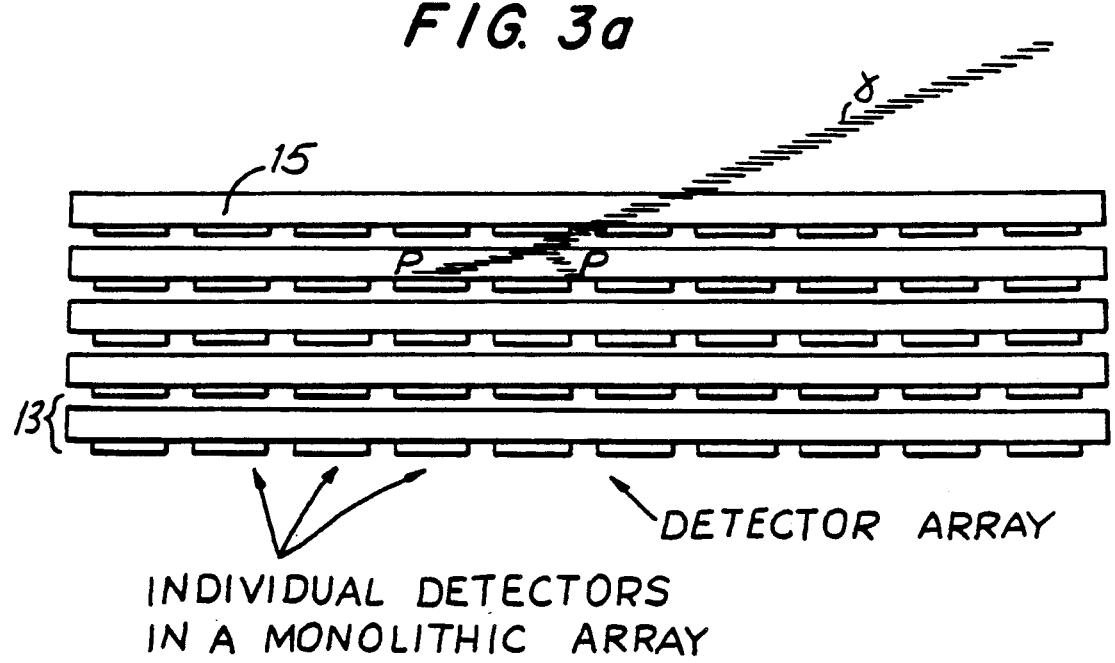
INDIVIDUAL DETECTORS
IN A MONOLITHIC ARRAY
DETECTOR ARRAY
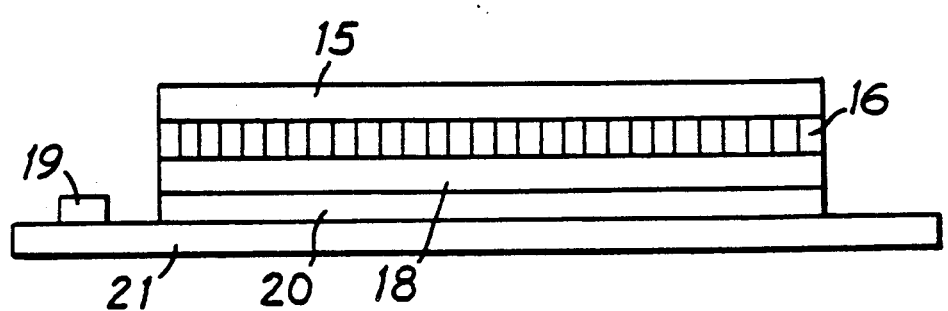
FIG. 3b

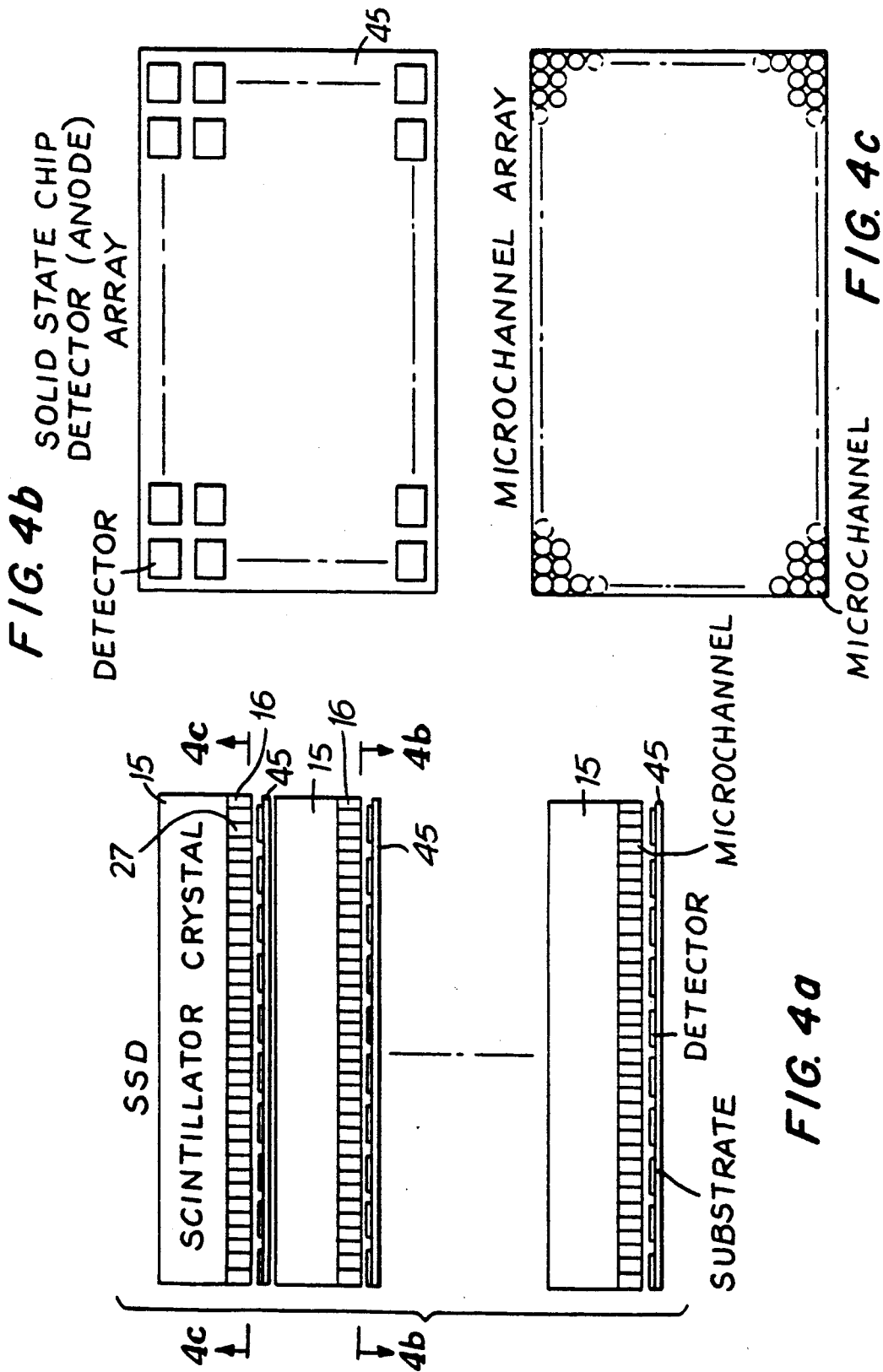

HIGH RESOLUTION POSITION SENSITIVE DETECTOR

BACKGROUND OF THE INVENTION

This invention relates to apparatus and methods for the identification of sources of nuclear radiation within objects that may be opaque to other radiation. More specifically this invention relates to a high spatial resolution gamma ray detector employing focal plane array technology and a novel scintillation crystal radiation detection device.

There is a current need to identify nuclear sources within structures that are opaque to most non-nuclear radiation. The identification must be capable of being made from a remote distance in a non-destructive manner. Military uses include the identification of nuclear space mines near ballistic missile defense satellites. A device capable of such identification is also useful for nuclear weapons treaty verification since nuclear weapons have very definite nuclear material configurations and the combination of information about the spatial distribution of nuclear material within an object together with information about the emitted gamma-ray spectrum is often sufficient to characterize an object as a container for a nuclear weapon. To accomplish such identification requires a resolution of roughly 2 cm which is beyond the capability of current sensors and gamma-ray telescopes for any practical distance of the sensor from the object.

The invention can also be used to distinguish nuclear weapon containing reentry vehicles from decoys, when used in conjunction with a pulsed neutron source. The neutrons cause the emission of gamma-rays from the heavy reentry vehicle material but pass through decoys without comparable amounts of such emission. The gamma-rays are detected and discriminated by the present invention.

OBJECT OF THE PRESENT INVENTION

It is an object of the present invention to provide a position sensitive high resolution detector for gamma-radiation.

It is a further object of the present invention to provide such a detector as a structure comprising a scintillator, a microchannel plate and a layer of anodes that respond to impinging radiation by changing the state of the anodes, together with electronics to read out the location of the anodes whose state has changed.

It is a still further object of the present invention to provide a position sensitive high resolution stacked detector formed from a stack of such individual detectors, wherein each detector layer provides the high resolution of a thin detector while the stack is deep enough to provide attenuation of incoming hard radiation.

It is an object of the present invention to provide a high spatial resolution gamma-ray camera for identifying nuclear material configurations.

It is a further object of the present invention to provide a high resolution position sensitive gamma-ray detector as a component of such a high resolution gamma-ray camera.

It is a further object of the present invention to provide such a device having high resolution and a high data rate with real time processing for use in nuclear imaging and nuclear monitoring.

It is a further object of the present invention to provide a gamma-ray camera for extra-atmospheric discrimination of reentry vehicles from decoys.

BRIEF DESCRIPTION OF DRAWINGS

FIG. 1a is a perspective view of the preferred embodiment of the high resolution camera of the present invention.

FIG. 1b is a perspective view of a nuclear source to be imaged by the high resolution camera of FIG. 1a.

FIG. 3a is a cut-away view of the position sensitive detector of the present invention.

FIG. 3b is a side view of an individual subsensor assembly.

FIG. 4a is a side view of the microchannel arrays of the present invention and their relation to the scintillator crystal and anode arrays.

FIG. 4b is a top view of a microchannel array of FIG. 4a.

FIG. 4c is a top view of an anode array of FIG. 4a.

FIG. 9b is a blow-up of a portion of the sensor array of anodes of FIG. 9a.

FIG. 11b is an enlargement of an area where four arrays meet in FIG. 11a.

FIG. 11c is an enlargement of an area at a corner of the array of FIG. 11a.

DESCRIPTION OF A PREFERRED EMBODIMENT OF THE INVENTION

Figure 2:
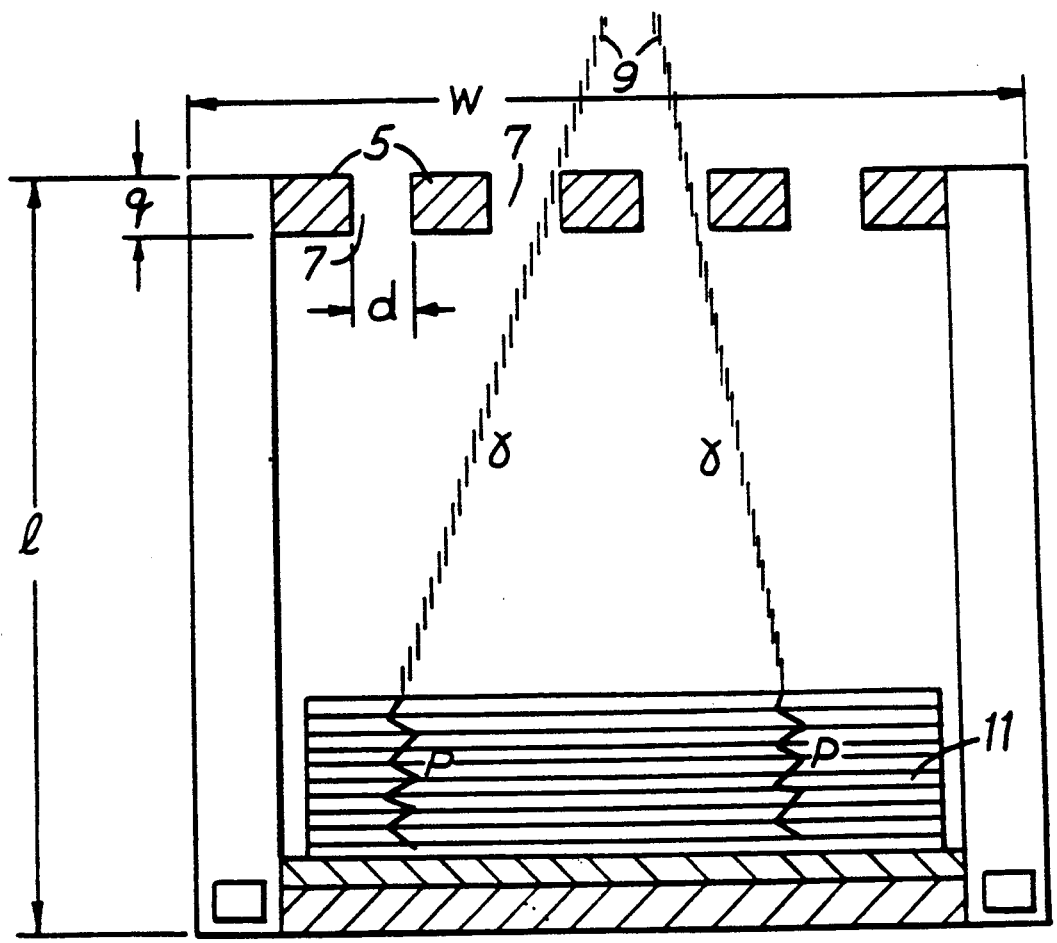
FIG. 2 is a cut-away view of a coded aperture gamma-ray camera of the present invention.

A preferred embodiment of the present invention is designed to sense gamma-ray photon energy on the order of 1 MeV (million electron volts) from a nuclear source. FIG. 1a depicts the overall device 1 as a high resolution gamma-ray "camera." In a preferred embodiment, the camera is 2.5 m long with an aperture 3 of 1 m$^2$. Assuming a minimum practical distance L from the camera 1 to the nuclear source object 3 (FIG. 1b) of 100 meters, a 2 cm resolution would be possible using the preferred embodiment and an exposure time of about 40 hours. If the distance L from the object to the sensor were 1 km and the length of the camera extended to 12.5 m, an exposure of 16 days would be required with aperture of 10 m².

FIG. 2 shows in more detail the high resolution camera 1 of the present invention. Key components of the sensor are a coded lead aperture mask 5 and a position sensitive high resolution detector 11.

As seen in FIG. 2 (not to scale), the lead mask 5 (about 2 cm thick) absorbs or scatters incident gamma-rays 9 not passing through the mask apertures 7. The mask 5 is essentially an array of "pinholes", in a pattern. A preferred pattern allowing half the mask area to be effective in collecting gamma-rays is known in the prior art as a Uniformly Redundant Array (URA) and allows the images from the different pinholes to be deconvolved from each other and effectively superimposed. See, e.g. Cook et al, *Gamma-Ray Imaging With A Rotating Hexagonal Uniformly Redundant Array*, Ns-31 IEEE Trans. on Nucl. Sci. 771-75 (1984).

The aperture of each pinhole should preferably "see" the whole target. However, the detector mask thickness, q, is preferably at least a gamma-ray range thick (about 2 cm of lead) to optimally modulate the photons. This means that the pinhole aperture is d/q radians and for d=0.05 cm the pinhole aperture is about 0.025 radians for a 2 cm thick lead mask. Radioactive sources of diameter up to about 2.5 m can therefore be seen at a range of L=100 m through each individual pinhole. In an alternative embodiment the mask may be concave (with the pinholes focused on the target) rather than flat to increase the efficiency of the mask.

In effect the camera is composed of a number of individual cameras with small apertures, all observing the source object. The angular resolution of the sensor is determined by the ratio of the aperture diameter d to the length of the sensor 1 (d/l radians=2×10 m for d=0.05 cm, l=2.5 m). The operational sensor resolution for object-sensor distances of 100 m is $2 \times 10^{-4}$ radians giving a spatial resolution of 2 cm at the source. (2 cm/100 m). This is about a factor of 50 better than current astronomical camera performance.

Critical to the operation of the camera is its high resolution detector. The position resolution of the detector is designed to be roughly equal to or better than the aperture hole diameter. The interaction position of individual gamma-rays 9 which have passed through the apertures in the mask is determined by the distribution of scintillator photons over detectors within the high resolution detector 11.

A background subtraction may be made on the basis of scintillators surrounding the instrument that are not specifically directed at the target.

The high resolution detector 11 uses an advanced focal plane array (FPA) technology, and a stacked scintillator crystal design. It is shown in detail in FIGS. 3a-6b. As shown in FIG. 3a, several subsensor assemblies 13 are stacked to form a detector. Each subsensor assembly 13 is a multi-layered, solid state, radiation hard structure. An individual subsensor assembly is depicted in FIG. 3b. It comprises a layered structure including a thin scintillator crystal slab 15 typically NaI (Tl) or Bismuth Germanate crystals, a microchannel plate amplifier array 16, a detector array of anodes 18, on a silicon-sapphire substrate 20, and a printed circuit board 21. The anodes can be made as small as necessary; the total scintillator thickness is maintained at a gamma-ray attenuation length (or more) while the highest resolution is achieved.

Figure 5B:
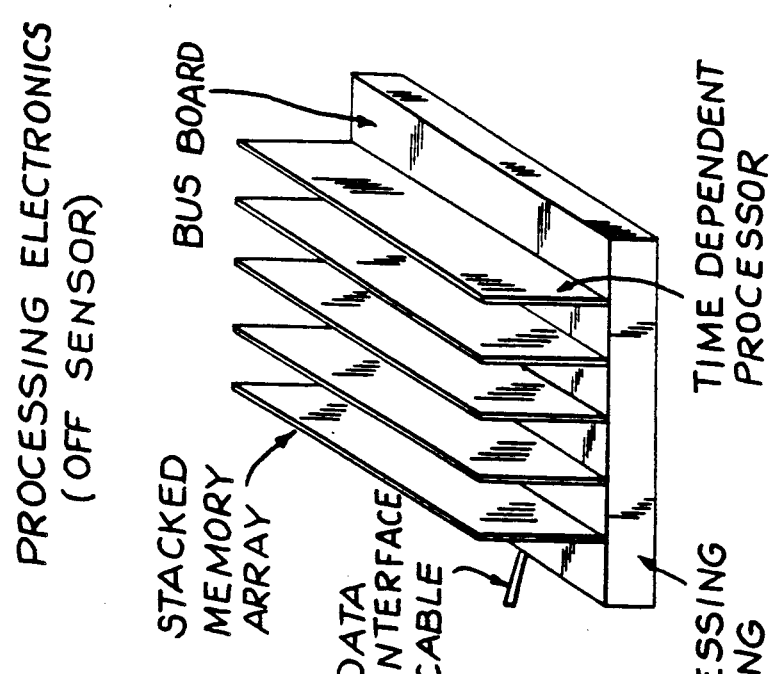
FIG. 5b is a perspective drawing of the off sensor processing electronics.
Figure 5A:
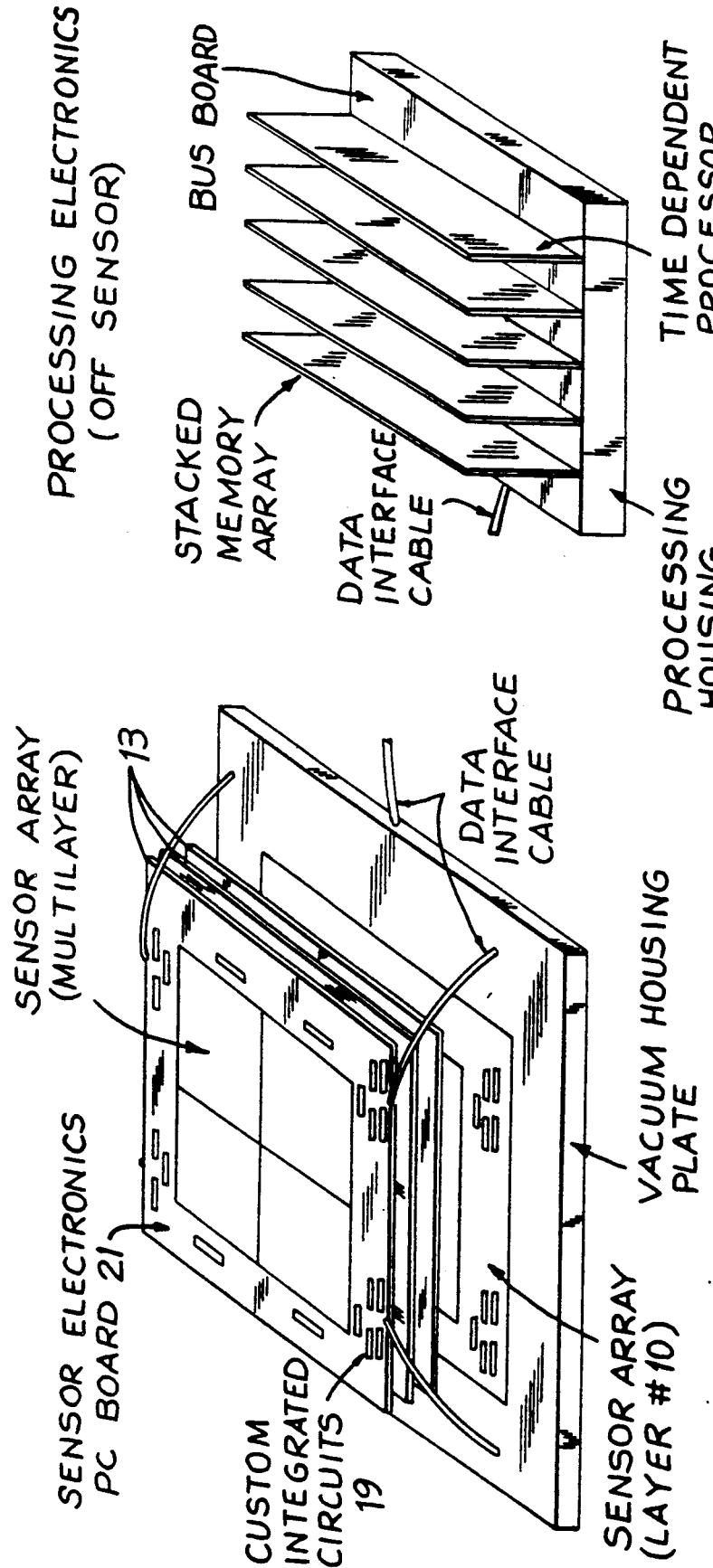
FIG. 5a is a perspective drawing of a portion of the high resolution detector of the present invention.

The high resolution detector as partially shown in FIG. 5a comprises 10 subsensor assemblies 13 mounted in a three dimensional evacuated structure (not shown). Separate integrated circuits 19 for each layer provide the necessary critical timing and signal conditioning for sensor operation of that layer. The electronics for each layer are mounted on a printed circuit board 21 surrounding that layer's detector anode arrays. As shown in FIGS. 5a and 9a-11c, it is preferred to construct the detector anode array as a 12×12 array of unit cells (see FIG. 9a) on 6.1 cm square substrates. These are then placed in an 8×8 pattern (see FIG. 11a) to form a quadrant of the detector anode array. Four quadrants form that array, which is therefore approximately a one square meter area on a single pc board termed the sensor electronics board.

The single multilayer sensors are stacked to obtain a high resolution, high efficiency, high energy particle measuring device. The inefficiency of a single layer due to the large particle range or inefficiency due to a thick scintillator is overcome. Stacking ordinary photomultiplier tubes is much less efficient because of their large size. The microchannel plate/anode combinations will only be 0.2 to 0.3 cm thick. This makes effective stacking possible.

Sensor array data processed by the sensor electronic board 21 is fed directly into an off-sensor processing unit. This unit stores array data into a stacked memory array for the Time Dependent Processor (TDP) (See FIG. 5b). The TDP calculates gamma-ray interaction positions and total energy in real time.

Figure 6A:
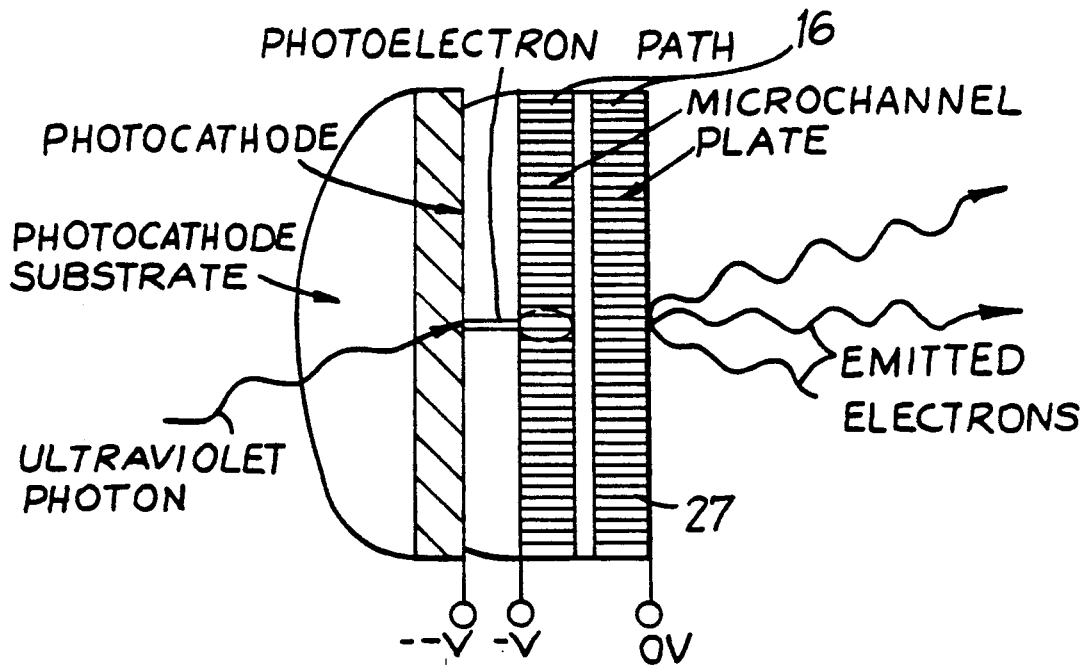
FIG. 6a is a cut-away view of a microchannel plate.
Figure 6B:
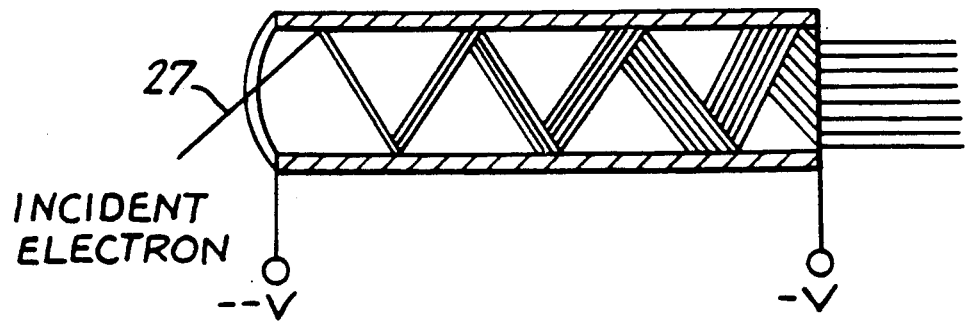
FIG. 6b is a blow-up of an element of the microchannel plate of the present invention.

The microchannel plate 16 of FIG. 3b is an array of small channel electron multipliers also shown in FIG. 6a used to amplify an electron beam containing spatial information. Many such channels stand over a single anode. A typical diameter of a single channel is $50 \times 10^{-4}$ cm. Each cylindrical channel 27 functions as a conventional photomultiplier tube. Each channel is a glass tube with its inner surface made semiconducting and will emit secondary electrons when bombarded with primary electrons accelerated in an electric field. Electrons enter the microchannel (See FIG. 6b) and strike the wall to produce secondary electrons which are accelerated axially along the channel by an electric field. The transverse energy of emission causes the electrons to cross the channel wall and produce more secondary electrons. This process is repeated until a large number of electrons emerge from the microchannel plate.

Under ordinary room temperature conditions thermal noise generated in the detectors could overwhelm the scintillator photon signal. Reduced temperature operation is avoided in the present invention by having the microchannel plates amplify the scintillation photons so the detector signals are well above the room temperature detector noise.

In operation radiation strikes a scintillator and produces photons that in turn produce electrons in the microchannel plate. These electrons neutralize a positive charge on the anode elements. In the unit cell associated with each of the anodes in FIG. 4b is a readout capacitor. The charge state of the anode is transferred to the capacitor and the anode is reset to its original charge state. The image of the nuclear source is thus contained in information of the location of the capacitors that contain information of an anode that received electrons from the microchannel plate.

A sensor chip 45 (see FIGS. 4a-b, 9a-11c) consists of a monolithic structure containing both the anode and readout (ARO) electronics. Each sensor chip is configured as a 12×12 anode element array shown in FIG. 9a. Center to center anode spacing is 5000μ (0.5 cm) with a dead space of 100μ between anodes. This dead space is used for the readout electronics. The anode area is 4950μ×4950μ as depicted in the blowup FIG. 9a. Overall chip size is about 6.1 cm×6.1 cm which is compatible with 4 inch (10 cm) diameter substrate wafers.

Figure 10:
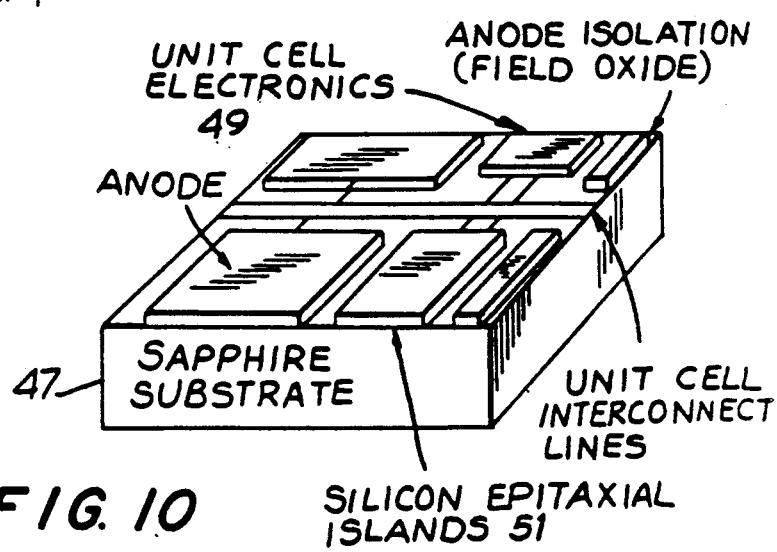
FIG. 10 is a drawing (not to scale) of the sensor chip unit cell structure.

A representative perspective drawing of the sensor chip monolithic structure is depicted in FIG. 10. The starting material 47 is silicon on sapphire (SOS) compatible with low capacitance anode construction and Complementary Metal Oxide Semiconductor (CMOS) technology. Both P-channel and N-channel transistors reduce gate propagation delay and power dissipation. The sensitivity of the sensor chip is determined by the value of the sense capacitor for each unit cell. The anode, because of its construction, is the dominant source for this capacitance. The construction of this capacitor on thick $SiO_2$ and sapphire reduces its value and increases the sensor chip sensitivity. The readout electronics 49 is constructed between each anode. Silicon epitaxial islands 51 serve as a readout substrate for the construction of both PMOS and NMOS transistors. Most of the space between the anodes is taken up by either the readout or the service lines to the readout.

Figure 11A:
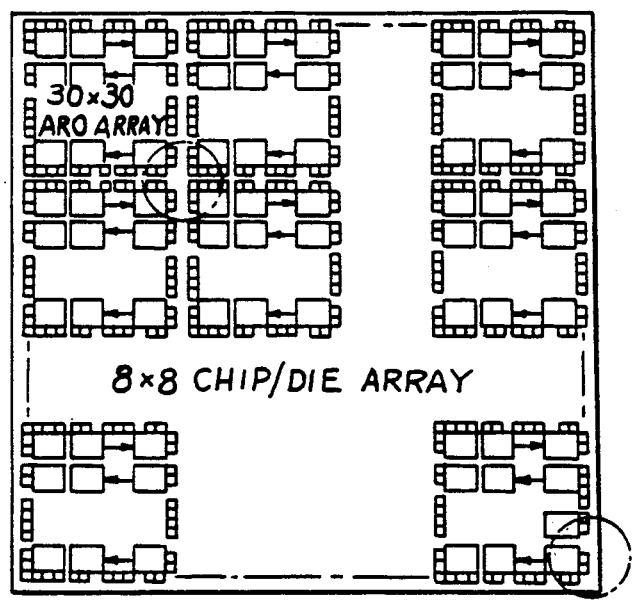
FIG. 11a is a top view showing the sensor chip array butting.
Figure 11B:
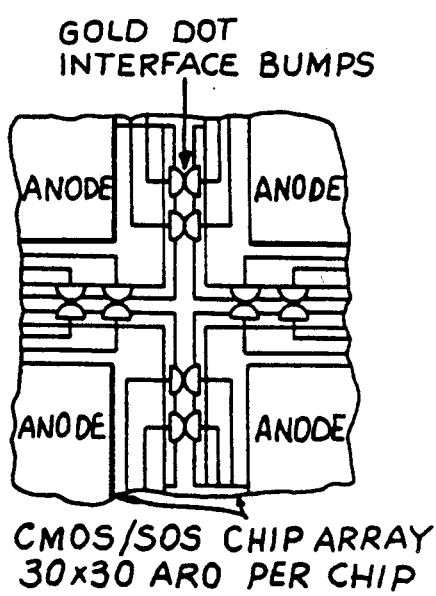
Figure 11C:
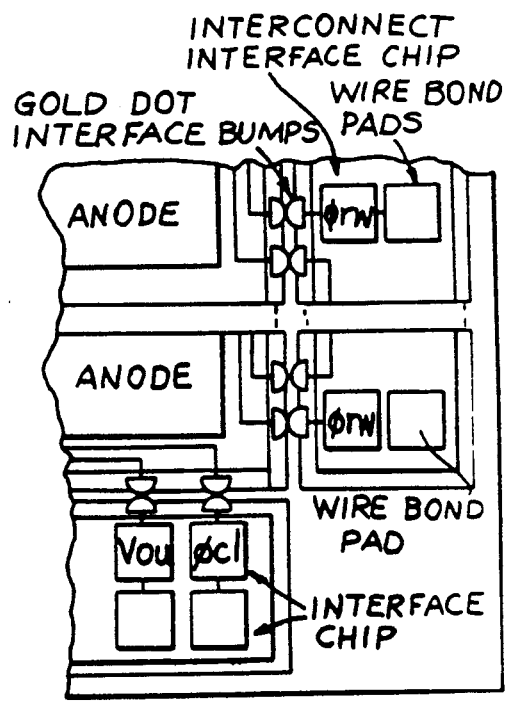

To address interfacing a large number of sensor chips and to minimize dead space, as illustrated in FIG. 11a for one layer and one quadrant, the preferred embodiment of the invention employs a merge of both gold dot technology and ceramic printed circuit lithography. All sensor chips are identical no matter where they are located in the array. Because of this a special interface chip is needed to communicate to the outside world (off-chip). Both the wire bond interface chip and the interconnect interface chip meet this requirement. The wire bond interface chip is used for electrical connection to the sensor PC board and associated electronics. The interface chip is used in a similar manner.

The electronic subsystem is partitioned into two functional units. The high resolution detector Sensor Board Electronics [SBE]FIG. 7 and the Off Sensor Processing Electronics [OSPE]FIG. 8 make-up these two units. The function of the SBE is to readout all stored data in the sensor array in real time and transfer it to the OSPE in digital form.

Figure 7:
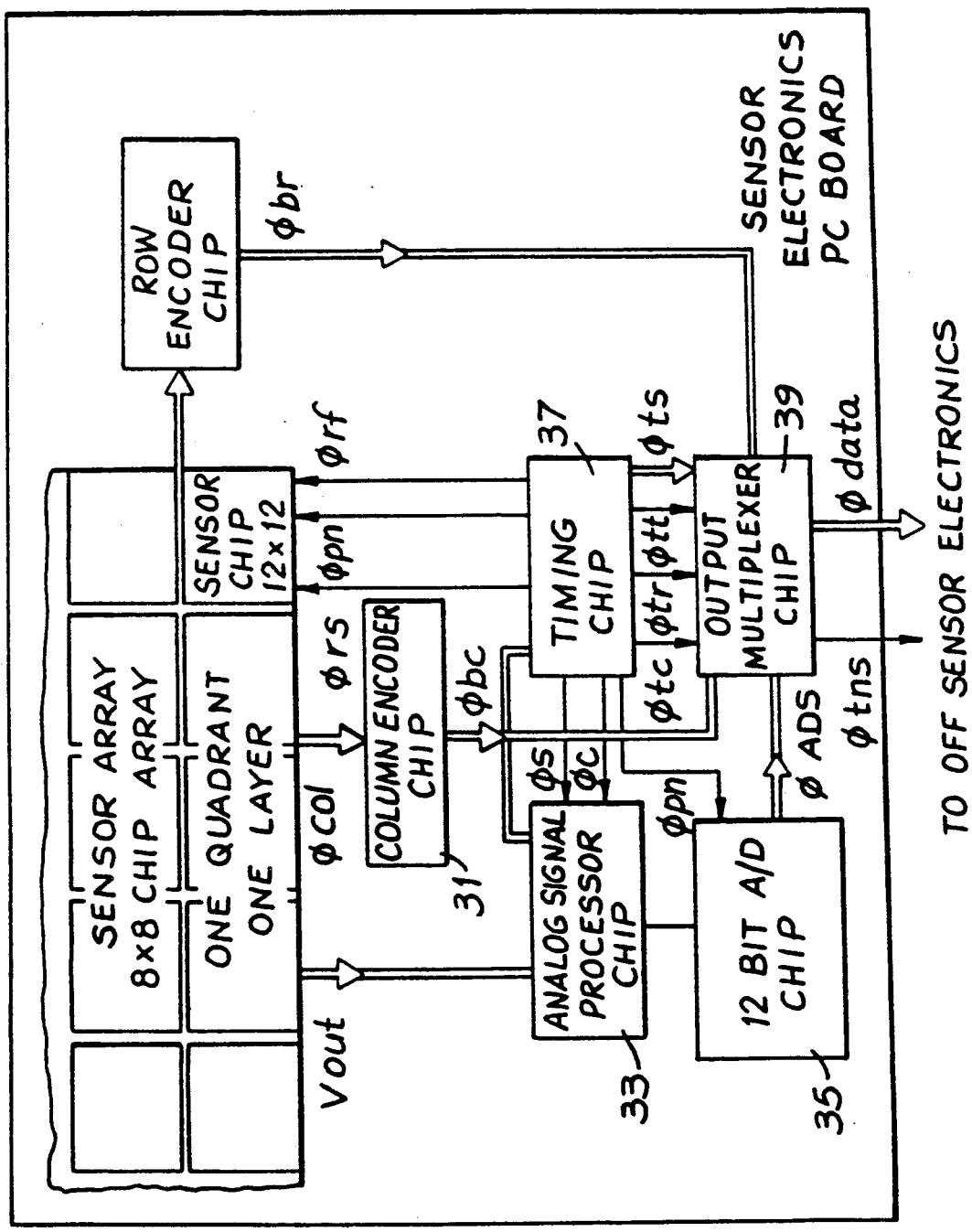
FIG. 7 is a schematic rendering of the Sensor Board Electronics of the present invention.

The SBE as depicted in FIG. 7 provides the necessary timing and signal conditioning to ensure this operation. Parallel processing is required at this level to meet the signal processing demands necessary for real time detection of incoming gamma-rays. This requirement is satisfied by providing each layer and quadrant with a unique real time processing SBE unit.

Referring to FIG. 7, the address encoder chip 31 assures that each anode/readout unit cell is uniquely identified by a 7 bit binary coded number. This encoder converts 96 bit addresses into a 7 bit binary coded address. The row (not shown) and column address encoders are functionally the same. The Analog Signal Processor (ASP) chip 33 conditions the output signal from the sensor array for the Analog to Digital (A/D) converter 35.

The functions of the ASP include signal buffering, clamp and sampling and output signal amplification.

The necessary timing to operate the sensor, ASP, A/D and the multiplexer chip are derived from the timing chip 37. This chip provides all of the required clocks to operate the SBE unit. The output of the ASP feeds into a 12 bit 10 MHz A/D converter. This gives the sensor a dynamic range of about a 4000 to 1. The output of the A/D will feed into the multiplexer chip 39. This chip tags and labels each set of data for later processing by the Time Dependent Processor (TDP) 41 on FIG. 8. A data set consists of four 20 bit words made up of the sensor row and column address, signal time stamp and the sensor signal. This chip also provides the required interface between the SBE and OSPE unit.

Figure 8:
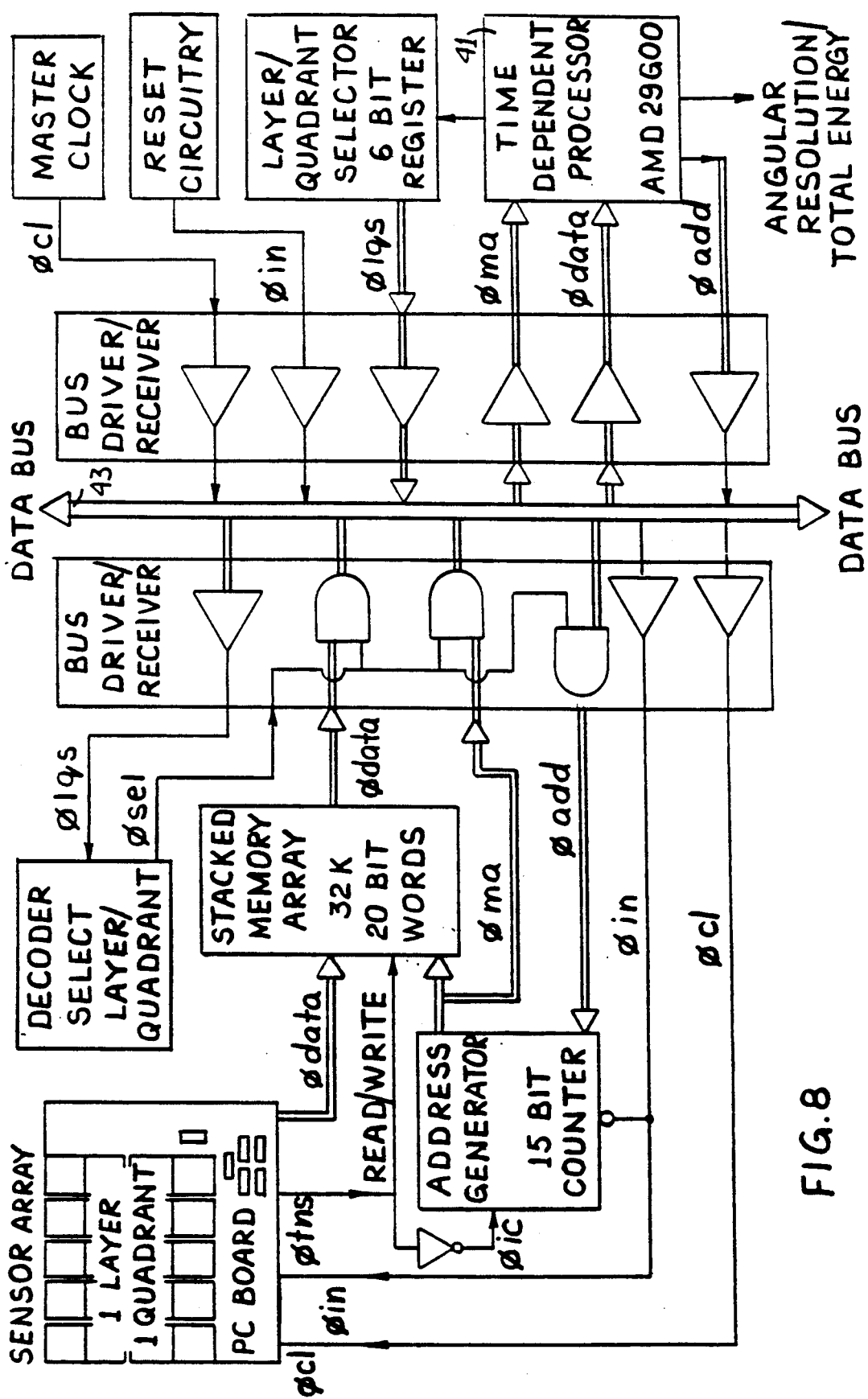
FIG. 8 is a schematic of the off-sensor processing electronics.
Figure 9A:
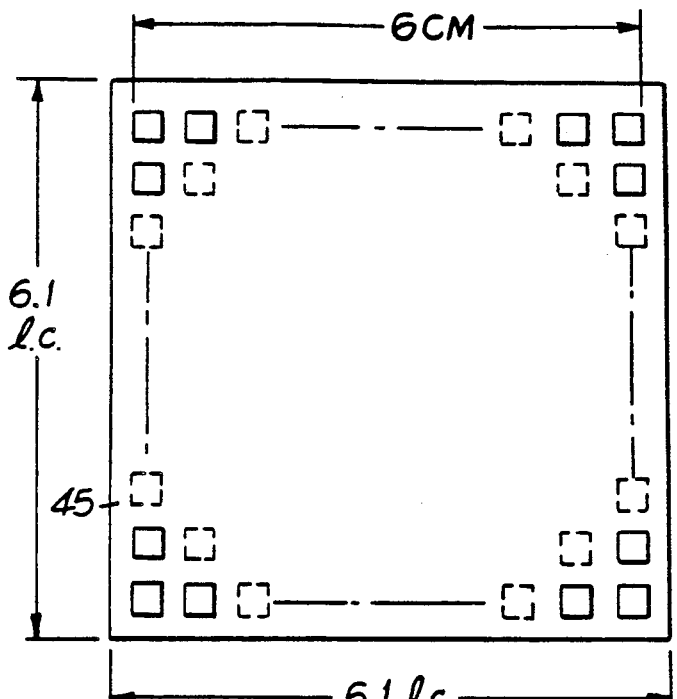
FIG. 9a is a top view of a sensor chip layout also termed a sensor array of anodes.
Figure 9B:
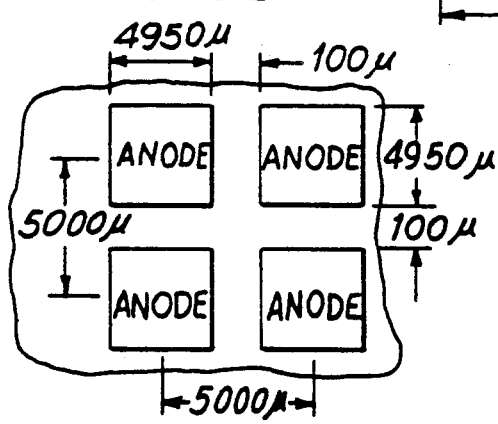

The OSPE (FIG. 8) unit has two primary functions, to store all incoming SBE unit data and to process this gamma-ray position and energy data in real time. Each SBE has its own memory assigned in the OSPE unit, as shown in FIG. 8 and FIG. 5a. All layer and quadrant memory is accessed by the TDP through a common data bus 43. Data from each layer and quadrant is uniquely addressed due to the label and tag method used. The TDP is a parallel processor tailored to meet the high processing data rates required in real time. This processor will analyze a massive amount of both sensor data and time stamp information.

Figure 12:
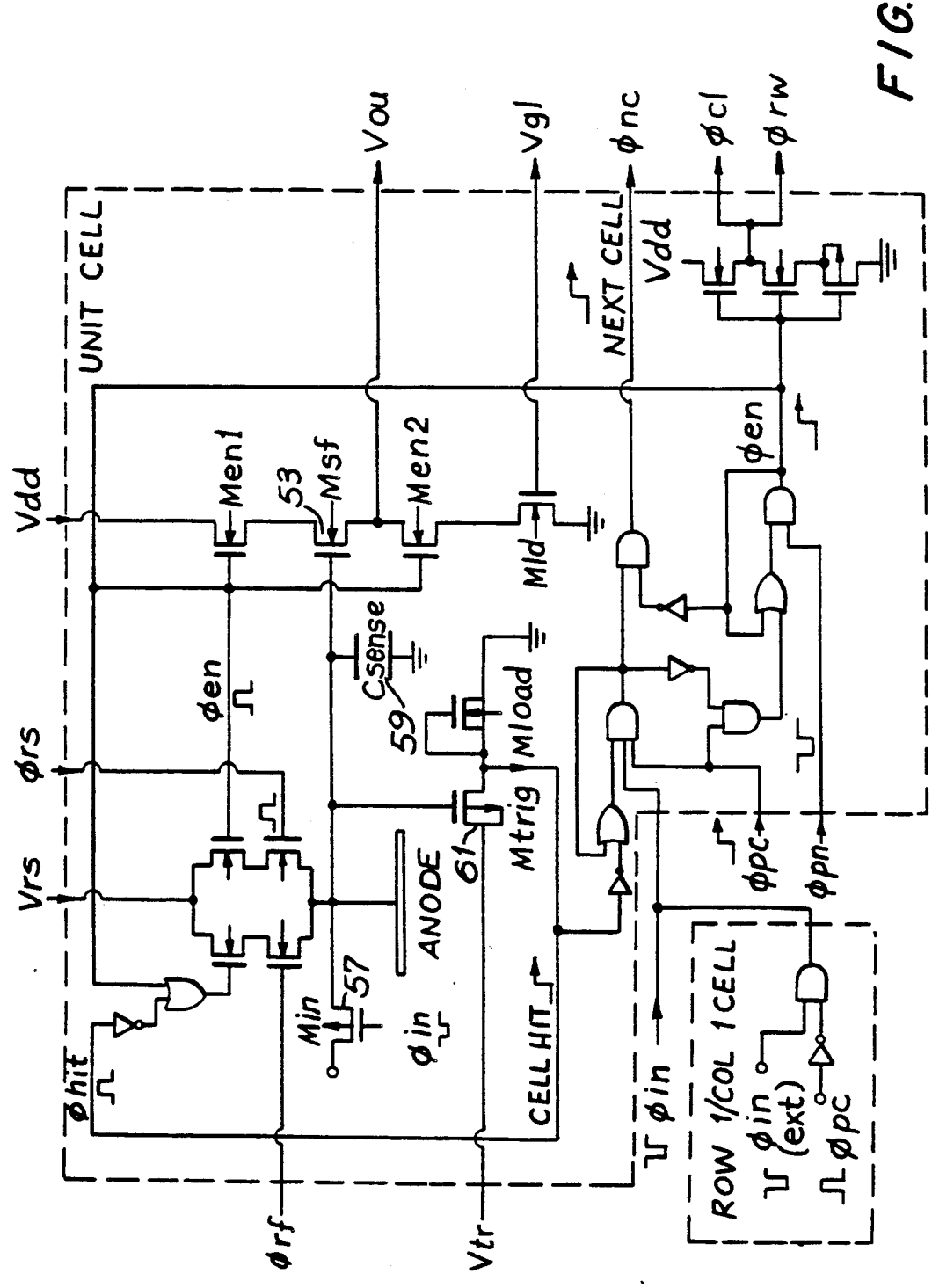
FIG. 12 is a schematic rendering at the gate level showing a unit cell electronics.

The basic purpose of the sensor chip unit cell circuit is to deliver the anode charge (signal) to the SBE unit in real time. The Anode/Readout (ARO) unit cell design chosen for the high resolution detector sensor is shown in FIG. 12.

The readout chip employs the direct readout approach which incorporates a switched capacitor per anode/readout. Unlike conventional readout circuits which require external address polling of each and every unit cell in the array, the ARO design provides the address of the unit cell in the sensor array to be serviced by the Sensor Board Electronics (SBE). Only the unit cells with valid data are serviced, allowing for a very large sensor array coupled with high data repetition rates. This approach is made possible by the high gains for the microchannel plates amplifying the sensor signal and allowing the unit cell to toggle logic identifying valid data.

Radiation hardening techniques are used in the construction of the readout design. This includes thin gate oxide, silicon on sapphire (SOS), complementary metal oxide semiconductor (CMOS) and an enhanced grounding scheme per unit cell. Total dose radiation hardening using these techniques is expected to be well over $10^6$ RAD-SI. Single event up-set in the readout design is not an issue for gamma fluxes of less than $10^{12}$ gammas/cm$^2$ sec.

Figure 13:
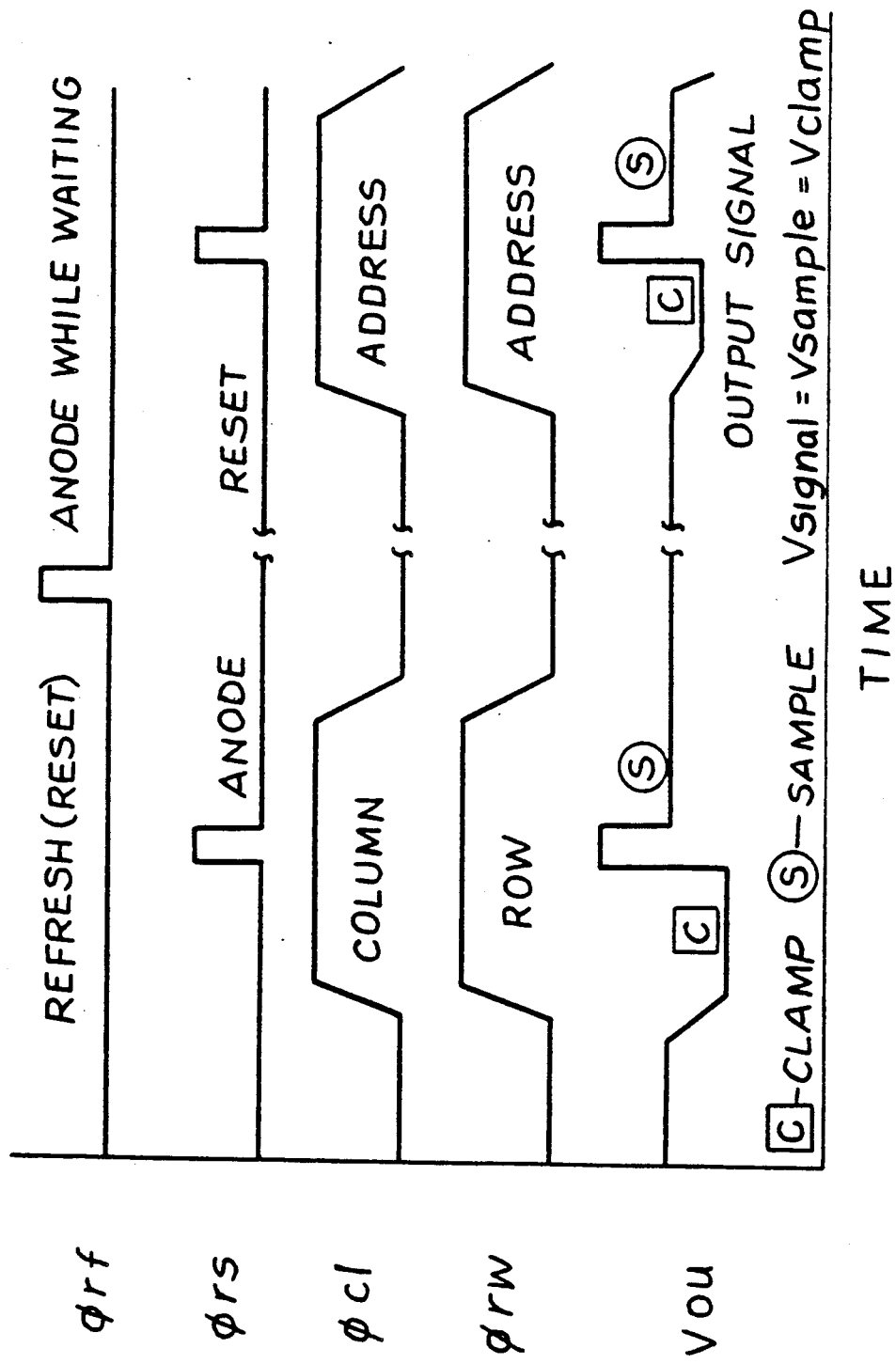
FIG. 13 is a timing chart for the electronics of the present invention.

The high resolution detector sensor employs a source follower per anode/readout to achieve low noise and wide dynamic range. During circuit initialization, the reset MOSFET (Min) 57 charges the sense capacitor 59 to a predetermined value (Vrs). FIG. 13 is a timing diagram of unit cell operation. The sense capacitor 59 is discharged by the anode when electrons from the microchannel plates strike the anode. The discharge capacitor turns on transistor (Mtrig) 61 generating a logical high state flagging the address polling logic to stop and service this unit cell. The internal address polling logic in the ARO chip is functionally very similar to a controlled ring oscillator. The address polling logic is initialized with a ($\phi$nc) of the next unit cell. In this way a serpentine polling chain is created.

At the end of the address polling sequence all unit cells are then reset in parallel to a logical zero to save time. This last action is unlike the function of a ring oscillator which would sequentially propagate to a logical zero. The address polling logic is stopped from propagating through any unit cell when a capacitor discharge has occurred. After servicing the unit cell, the address polling logic is allowed to propagate or poll the next unit cell when a $\phi$pn done pulse is given. The speed at which address polling occurs per unit cell is about 1 ns which is determined by the gate propagating time through two AND gates using layout rules for 1 Micron gate transistors. During unit cell servicing due to capacitor discharge, the unit cell source follower (Msf) 53 is enabled by the polling logic along with the row and column address. The timing chip 37 (See FIG. 7) on the SBE starts to generate the correct sequence of timing in preparation for unit cell readout. The voltage on the sense capacitor (Vou) is processed by the Analog Signal Processor (ASP) 33 with timing supplied by the timing chip 37. The voltage on the sense capacitor 59 is first sampled then reset to its previous value (Vrs) and its voltage is sampled again. This cycle is repeated for each row and column requiring service. The difference in the output (Vou) shortly before and after reset is proportional to the charge build-up on the anode. The time required to service a unit is approximately 125 ns which is dictated by the speed of the 10 MHz A/D.

It is periodically necessary to service the unit cells when a capacitor discharge has not occurred in a set period of time. The anode will discharge naturally due to a reverse junction leakage current from transistors connected to the anode. This action is circumvented by periodically resetting the anode between sense capacitor discharges. This action is known as refreshing the unit cell. Power dissipation per ARO is kept to a minimum because only one unit cell is selected at any given time.

Another embodiment of this invention is as a gamma-ray camera for extra-atmospheric discrimination of reentry vehicles form decoys.

One of the major problems for the mid-course and terminal phases of a layered ballistic missile defense (BMD) is the discrimination of warhead carrying reentry vehicles (RV's) from decoys. The expected decoy to RV ratio is more than 100 to 1. Given the energy and time required to destroy each RV or decoy, a BMD could be overwhelmed by "realistic" decoys. Even if the decoys did not simulate the possible infrared, radar or dynamic RV signature, a large number of decoy objects could act as traffic decoys, saturating the processing and battle management capabilities of a defense. Most mid-course decoys are expected to be light (on the order of one kg or less) because of the ease of putting light objects into orbit and their expected effectiveness as simulation and traffic decoys. Some are expected to be heavier, thwarting terminal phase BMD. If light decoys could rapidly be discriminated from RVs a successful mid-course BMD is more possible. Additionally, if heavy decoys can be discriminated from RVs in midcourse, the effectiveness of both mid-course and terminal BMD would be substantially increased.

To accomplish the RV/decoy discrimination using a pulsed neutron source, requires a gamma-ray camera of very high spatial resolution and the capability of rapidly storing a very large amount of data for later processing. Most of the data is background generated by the pulsed neutron source.

In this case the diameter of the anode is varied along with the thickness of the scintillator crystal. For example, in the case of the previous embodiment scintillator slabs were 0.5 cm thick so the anodes in FIG. 9b were 0.5 cm wide. For reentry vehicle decoy discrimination the preferred thickness of the scintillator slabs is 0.2 cm and the anodes are 0.2 cm wide. This affects both the anode dimensions and the number of anodes per chip, since chip size remains preferably at about 6 cm.

The main differences between the RV/decoy discrimination application and the nuclear source imaging application in that although the sensor is the same, the gamma-ray flux of the RV/decoy application is too high to measure in real time even with the polling technique of the present invention. Instead, the data is stored for each successive gamma-ray interaction on 100 on-chip capacitors, in the unit cell, under the anode (not shown but on the other side of the substrate in FIG. 10). Each gamma-ray interaction causes a charge to be built up on the anode and is immediately generated by the next gamma-ray. Since the gamma-rays arrive in a narrow time window (like $10^{-4}$ sec) 100 capacitors are sufficient.

In the nuclear imaging application, it was preferred to read out the anode charge as the gamma-ray interaction occurred (this may be over a time period of days). The RV/decoy application changes the unit cell electronics as shown in FIG. 14 and the timing FIG. 15.

Figure 14:
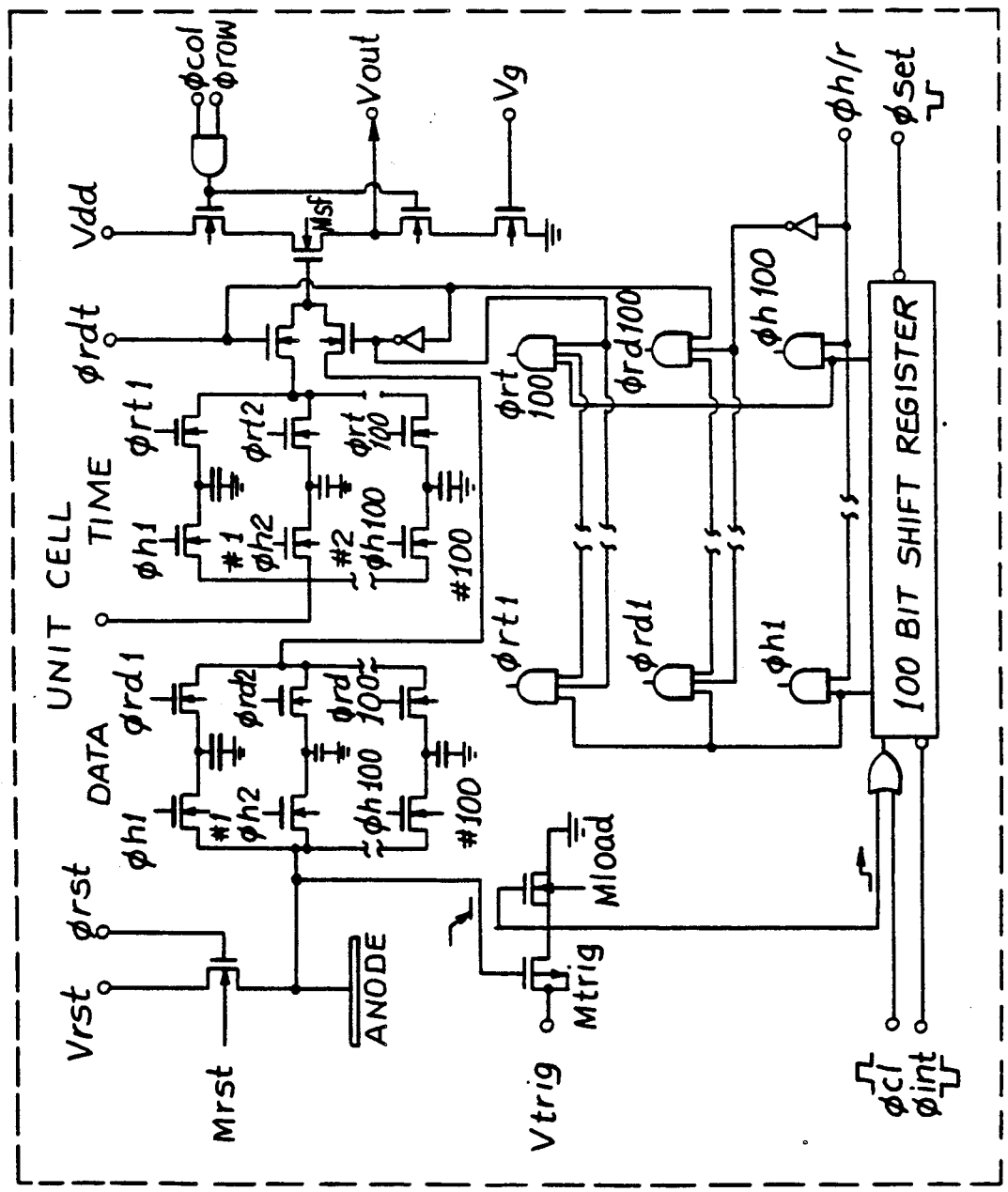
FIG. 14 is a schematic rendering at the gate level showing a unit cell electronics for an embodiment adapted to decoy discrimination from reentry vehicles.
Figure 15:
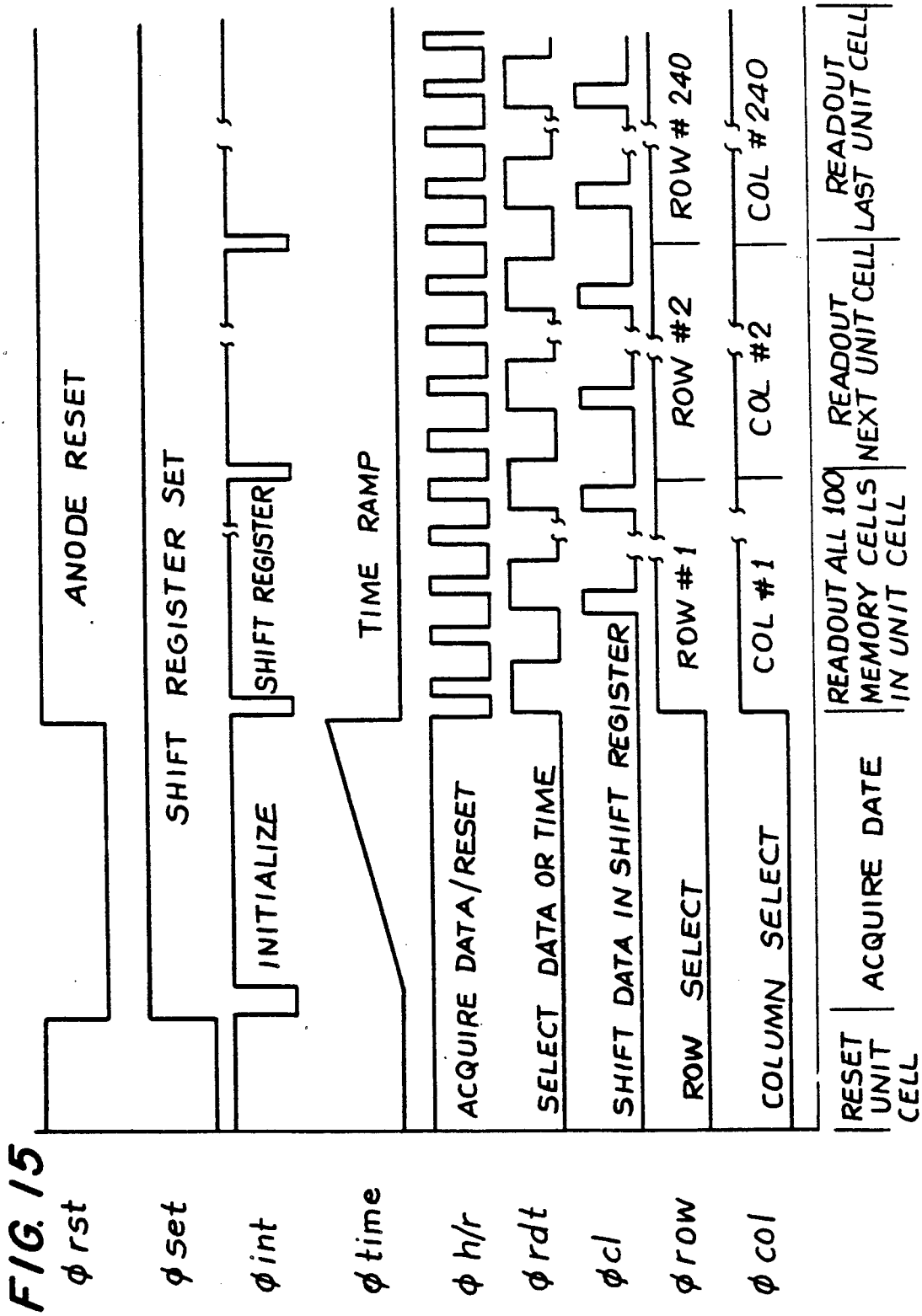
FIG. 15 is a timing chart for the electronics of the present invention adapted to decoy discrimination from reentry vehicles.

Referring to FIG. 14 and 15, the readout chip employs the direct readout approach which incorporates a multiple switched capacitor per anode/readout. Because of the extremely high gamma/data rate all anode signal data will be stored along with its associated time stamp. The stamp will be used by the time dependent processor (TDP) to correlate data in other unit cells, quadrants and layers. Each unit cell preferably has a memory capacity for 100 data samples and 100 associated time stamps. All paired data (data/time stamp) are preferably read out at the end of the allocated data acquisition time. Radiation hardening techniques will be used in the construction of the readout design. This preferably includes thin gate oxides, silicon on sapphire (SOS), complementary metal oxide semiconductor (CMOS) and an enhanced grounding scheme per unit cell. Total dose radiation hardening using these techniques is expected to be well over $10^6$ RAD-SI The sensor employs a source follower per anode readout and multiplexer circuitry to achieve low noise and wide dynamic range. During circuit initialization, the reset MOSFET (Mrst) charges the sense capacitors (1 through 100) to a predetermined value (Vrst) (FIG. 13 shows the preferred unit cell timing diagram.) This is accomplished by setting the 100 bit shift register to the on state by clocking ($\phi$set) allowing all sense capacitors to be reset as indicated above. During this time all time stamp capacitors are also initialized to a predetermined value. When the sensor is activated (Mrst) is turned off and $\phi$int is pulsed (10 ns) to initialize all unit cell logic. Initialization pulse ($\phi$int) sets all logic in the shift register to the off state except for bit #1 which is on. The time stamp reference voltage ($\phi$time) is slowly ramped up in time during data acquisition. The sense capacitor selected is discharged by electrons from the microchannel plates reacting to a gamma hit in the sodium iodide crystals. The sense capacitor discharge causes the shift register to be clocked (bit position #1 shifted to bit position #2). This has the effect of deselecting the current sense capacitor (#1) and selecting the next sequential sense capacitor (#2). Time stamp capacitor (#1) is also deselected and time stamp capacitor (#2) is now selected. The time stamp voltage on this capacitor is directly related to time since it is ramping up in time. This process is repeated for all acquired data until the sensor is deactivated. Transistor (Mrst) will at deactivation time be turned on preventing any further data acquisition All acquired data is thus stored in the capacitors and must be read out. The initialization pulse ($\phi$int) is activated to reset the shift registers in all unit cells in preparation for data readout. The desired row and column is selected allowing either data or its associated time stamp to appear at Vout depending on the state of ($\phi$rdt).

During data acquisition the unit cell source follower (Msf) is enabled and the voltage on the selected capacitor is sampled by the Analog Signal Processor (ASP). The sense capacitor is then reset to its previous value reset value and its voltage is sampled again by the ASP. This cycle is repeated for all data read out. The difference in the output (Vout) shortly before and after reset is proportional to the charge on the anode. The next sequential sense capacitor is selected by pulsing the clock line ($\phi$cl). This process is repeated for all 100 sense capacitors in the unit cell. The next row and column is selected and the process is repeated as before until all data is read out. In the RV/decoy discrimination application, the gamma-ray camera is deployed at a distance of about 1000 km from the RV/decoy cloud. The camera would have an angular resolution of $2 \times 10^{-4}$ radians and localize an RV within 40 microradians. If the camera length was 10 m the angular resolution would be $5 \times 10^{-5}$ radians and the source localization would be about 10 microradians.

A still further embodiment of the present invention is as a portable x-ray machine using a single scintillator layer of this invention. A preferred size is that of a book. This embodiment functions as a portable stealth camera for taking pictures of the inside of a sealed container and storing the information on on-chip capacitors for later analysis. The x-ray source (actually low energy gamma-rays) would be a small piece of radioactive material or material rendered radioactive.

Although the predominant application is with x-rays and gamma-rays (25 KeV to 25 MeV) any radiation can be detected with the microchannel plate/anode technology of the present invention as long as it produces light in scintillatory crystals—which any charged particle will do—or electrons—in which case the microchannel plate does not require a photoelectric element.

I claim:

1. A position sensitive high resolution detector, said detector comprising as layers
   a scintillator,
   a microchannel plate amplifier array optically coupled to said scintillator and comprising a plurality of microchannels, each microchannel having a diameter substantially less than the resolution of said detector, and comprising a photocathode and a surface adapted to emit secondary electrons when bombarded with primary electrons,
   a layer comprising one or more sensor chips each adapted to receive electrons from said microchannel plate amplifier and comprising
   a substrate, and
   a sensor array of anodes on said substrate, each anode adapted to change state in response to the emission of electrons from adjoining channels of said microchannel plate amplifier,
   said detector further comprising sensor electronics adapted to read out data indicative of the location of the anodes whose state has changed.

2. The position sensitive high resolution detector of claim 1, wherein said sensor electronics is adapted to read out said data in real time.

3. The position sensitive high resolution detector of claim 1, wherein said sensor chips each comprise a plurality of sensor unit cells, each unit cell comprising an anode and electronic means to provide an anode charge signal for receipt by an off chip portion of said sensor electronics in real time.

4. The position sensitive high resolution detector of claim 3, said unit cell further comprising a signal storage capacitor, wherein said capacitor is adapted to store a signal indicative of the state of the anode.

5. The position sensitive high resolution detector of claim 4 further comprising electronic means to reset said anode after a signal indicative of the state of the anode is stored on said signal storage capacitor.

6. The position sensitive high resolution detector of claim 1 wherein said sensor electronics is adapted directly to read out said data.

7. The position sensitive high resolution detector of claim 1 wherein said layers are contained in a vacuum housing.

8. The position sensitive high resolution detector of claim 1 wherein said plurality of sensor chips laterally terminate in dot interface bump means for making electrical connection between adjacent sensor chips.

9. The position sensitive high resolution detector of claim 8, wherein said sensor arrays comprise sectors of electrically connected adjacent sensor chips and each sector further comprises pad interface chips contacting dot interface bump means on the periphery of said sector, said pad interface chips adapted to facilitate bonding to wire.

10. The position sensitive high resolution detector of claim 1 wherein said substrate comprises silicon on sapphire.

11. A position sensitive high resolution stacked detector, said stacked detector comprising a plurality of layers of subsensor assemblies each comprising as layers
    a scintillator,
    a microchannel plate amplifier array optically coupled to said scintillator and comprising a plurality of microchannels, each microchannel having a diameter less than the resolution of said detector, and comprising a photocathode and a surface adapted to emit secondary electrons when bombarded with primary electrons,
    a layer comprising a plurality of sensor chips each adapted to receive electrons from said microchannel plate amplifier and comprising
    a substrate, and
    a sensor array of anodes on said substrate, each anode adapted to change state in response to the emission of electrons from adjoining channels of said microchannel plate amplifier,
    said detector further comprising sensor electronics adapted to read out data indicative of the location of the anodes whose state has changed, and
    said scintillators having a total thickness of at least about the attenuation length for gamma-rays traversing said individual scintillators.

12. The position sensitive high resolution detector of claim 11, wherein said sensor electronics is adapted to read out said data in real time.

13. The position sensitive high resolution detector of claim 11, wherein said sensor chips each comprise a plurality of sensor unit cells, each unit cell comprising an anode and electronic means to provide an anode charge signal for receipt by an off chip portion of said sensor electronics in real time.

14. The position sensitive high resolution detector of claim 13, said unit cell further comprising a signal storage capacitor, wherein said capacitor is adapted to store a signal indicative of the state of the anode.

15. The position sensitive high resolution detector of claim 14 further comprising electronic means to reset said anode after a signal indicative of the state of the anode is stored on said signal storage capacitor.

16. The position sensitive high resolution detector of claim 11 wherein said sensor electronics is adapted to read out said data in digitized form and in real time.

17. The position sensitive high resolution detector of claim 11 wherein said layers of subsensor assemblies are contained in a vacuum housing.

18. The position sensitive high resolution detector of claim 11 wherein said plurality of sensor chips laterally terminate in dot interface bump means for making electrical connection between adjacent sensor chips.

19. The position sensitive high resolution detector of claim 18, wherein said sensor arrays comprise a sector of electrically connected adjacent sensor chips and each sector further comprises pad interface chips contacting dot interface bump means on the periphery of said sector, said pad interface chips adapted to facilitate bonding to wire.

20. A high resolution gamma-ray camera for imaging a nuclear radiation source comprising
an aperture mask adapted to absorb or scatter gamma-rays not passing through apertures in said mask, and
a position sensitive high resolution stacked detector, said stacked detector comprising a plurality of layers of subsensor assemblies each comprising as layers
a scintillator,
a microchannel plate amplifier array optically coupled to said scintillator and comprising a plurality of microchannels, each microchannel having a diameter less than the resolution of said detector, and comprising a photocathode and a surface adapted to emit secondary electrons when bombarded with primary electrons,
a layer comprising a plurality of sensor chips each adapted to receive electrons from said microchannel plate amplifier and comprising
a substrate, and
a sensor array of anodes on said substrate, each anode adapted to change state in response to the emission of electrons from adjoining channels of said microchannel plate amplifier,
said detector further comprising sensor electronics adapted to read out data indicative of the location of the anodes whose state has changed, and
said scintillators having a total thickness of at least about the attenuation length for gamma-rays traversing said individual scintillators.

21. The high resolution gamma-ray camera of claim 20, wherein said sensor electronics comprises
a sensor electronics board comprising integrated circuitry adapted to read out said data in digitized form to off sensor processing electronics, said sensor electronics board comprising address encoder means to uniquely identify by an address each anode means,
an interface between said sensor electronics board and said off sensor processing electronics,
off sensor processing electronics adapted to store sensor board electronics unit data and to process gamma ray position information.

22. The high resolution gamma-ray camera of claim 21, wherein said sensor electronics is adapted to read out and to process gamma-ray position information in real time.

23. The high resolution gamma-ray camera of claim 21, wherein said sensor chips each comprise a plurality of sensor unit cells, each unit cell comprising an anode and electronic means to provide an anode charge signal for receipt by an off chip portion of said sensor electronics in real time.

24. The high resolution gamma-ray camera of claim 23, said unit cell further comprising a signal storage capacitor, wherein said capacitor is adapted to store a signal indicative of the state of the anode.

25. The high resolution gamma-ray camera of claim 24 further comprising electronic means to reset said anode after a signal indicative of the state of the anode is stored on said signal storage capacitor.

26. The high resolution gamma-ray camera of claim 23, wherein said electronic means is formed on an epitaxial island adjacent said anode.

27. The high resolution gamma-ray camera of claim 21 wherein said sensor electronics is adapted to read out said data in digitized form and in real time.

28. The high resolution gamma-ray camera of claim 21 wherein said layers of subsensor assemblies are contained in a vacuum housing.

29. The high resolution gamma-ray camera of claim 21 wherein said plurality of sensor chips laterally terminate in dot interface bump means for making electrical connection between adjacent sensor chips.

30. The high resolution gamma-ray camera of claim 29, wherein said sensor arrays comprise a sector of electrically connected adjacent sensor chips and each sector further comprises pad interface chips contacting dot interface bump means on the periphery of said sector, said pad interface chips adapted to facilitate bonding to wire.

31. The high resolution gamma-ray camera of claim 21, wherein said scintillator is a crystal of NaI or Bismuth Germinate.

32. The high resolution gamma-ray camera of claim 21, wherein said sensor electronics board comprises integrated circuitry to read out all stored data in a sector of said sensor array in real time in digitized form to off sensor processing electronics for timing and signal conditioning for sensor operation, said sensor electronics board comprising
an address encoder chip to uniquely identify each anode means,
a signal processor chip to condition an output from the sensor array for digital conversion,
a timing chip, and
a multiplexer chip to tag and label each set of data for later processing by a time dependent processor and to provide an interface between the sensor electronics board and an off sensor processing electronics unit,
said off sensor processing electronics unit adapted to store all incoming sensor board electronics unit data and to process the data and gamma ray position in real time and comprising
memory for each sensor board electronics.

33. A method for imaging at high resolution a source of radiation capable of producing photons in a scintillator comprising
   passing said source of radiation into a scintillator,
   passing said photons into a portion of a microchannel plate amplifier comprising a plurality of microchannels each having a diameter substantially less than said resolution and thereby causing electrons to be emitted from said portion of microchannels,
   receiving the electrons from the microchannel plate amplifier on a portion of a sensor array of anodes on a substrate, whereby the state of said anodes that receive the electrons is changed,
   reading out data indicative of the location of the anodes whose state has changed and forming an image of the source from said data.

34. The method for imaging at high resolution a source of radiation of claim 33 wherein the step of reading out data is done in real time.

35. The method for imaging at high resolution a source of radiation of claim 33 wherein a signal indicative of the state of the anode is stored in a signal storage capacitor.

36. The method for imaging at high resolution a source of radiation of claim 35 wherein the anode is reset after a signal indicative of the state of the anode is stored on said signal storage capacitor.

37. The method for imaging at high resolution a source of radiation of claim 33 wherein the step of reading out data is done in digitized form and in real time.

38. The method of producing a high resolution image of a nuclear radiation source within an object comprising
   causing gamma radiation from said source to fall on an aperture mask and passing gamma-rays through apertures in said mask
   passing said source of radiation into a stacked detector comprising a plurality of scintillators,
   passing photons from each of said scintillators into a portion of a microchannel plate amplifier associated with each scintillator, each microchannel plate comprising a plurality of microchannels having a diameter substantially less than said resolution and thereby causing electrons to be emitted from said portions of said microchannels,
   receiving the electrons from the respective microchannel plate amplifiers on a portion of a sensor array of anodes on a substrate associated with each scintillator, whereby the state of said anodes that receive the electrons is changed,
   reading out data indicative of the location of the anodes whose state has changed and forming an image of the source from said data.

39. The method of producing a high resolution image of a nuclear radiation source of claim 38 wherein the step of reading out data is done in real time.

40. The method of producing a high resolution image of a nuclear radiation source of claim 38 wherein a signal indicative of the state of the anode is stored in a signal storage capacitor.

41. The method of producing a high resolution image of a nuclear radiation source of claim 40 wherein the anode is reset after a signal indicative of the state of the anode is stored on said signal storage capacitor.

42. The method of producing a high resolution image of a nuclear radiation source of claim 38 wherein the step of reading out data is done in digitized form and in real time.

43. The method of producing a high, resolution image of a nuclear radiation source of claim 38 wherein said reading out of data comprises reading out all stored data in a sector of said sensor array in real time in digitized form to off sensor processing electronics for timing and signal conditioning for sensor operation, comprising the steps of uniquely identifying each anode means, conditioning an output from the sensor array for digital conversion, and labeling each set of data for later processing by a time dependent processor, and storing all incoming sensor board electronics unit data and processing the data in real time.

44. A position sensitive high resolution detector having processing electronics for a sensor array of anodes adapted to store data in response to an emission of electrons and to provide the data to an image recording means comprising
   address polling electronics adapted to sequence through every anode and to provide signals identifying those anodes having data,
   readout electronics adapted to respond to said identifying signals from said address polling electronics and to provide an address for each anode having data, and
   output electronics adapted to provide to the image recording means the data from each anode corresponding to the address provided by said readout electronics.

45. The position sensitive high resolution detector of claim 44 further comprising capacitive storage means to temporarily store the data for those anodes identified by said readout electronics.

* * * * *